(12) United States Patent
Yang et al.

(10) Patent No.: US 12,398,365 B2
(45) Date of Patent: Aug. 26, 2025

(54) LACTIPLANTIBACILLUS PLANTARUM FOR DEGRADING TANNINS AND SAPONINS, AND USE THEREOF

(71) Applicants: GUIZHOU UNIVERSITY, Guiyang (CN); CHINA AGRICULTURAL UNIVERSITY, Beijing (CN)

(72) Inventors: Fuyu Yang, Beijing (CN); Ningwei Wang, Beijing (CN); Kuikui Ni, Beijing (CN); Gang Xu, Beijing (CN); Hongzhang Zhou, Beijing (CN)

( * ) Notice: Subject to any disclaimer, the term of this patent is extended or adjusted under 35 U.S.C. 154(b) by 0 days.

(21) Appl. No.: 18/664,876

(22) Filed: May 15, 2024

(65) Prior Publication Data
US 2025/0027034 A1    Jan. 23, 2025

(30) Foreign Application Priority Data
Jul. 18, 2023    (CN) .......................... 202310881780.4

(51) Int. Cl.
| | |
|---|---|
| C12N 1/20 | (2006.01) |
| A23K 10/18 | (2016.01) |
| A23K 10/30 | (2016.01) |
| C12R 1/25 | (2006.01) |

(52) U.S. Cl.
CPC .............. *C12N 1/205* (2021.05); *A23K 10/18* (2016.05); *A23K 10/30* (2016.05); *C12R 2001/25* (2021.05)

(58) Field of Classification Search
CPC ........ C12N 1/205; A23K 10/30; A23K 10/18; C12R 2001/25
See application file for complete search history.

(56) References Cited

U.S. PATENT DOCUMENTS

2019/0054128 A1*    2/2019    Lebeer ................... A61P 31/04

FOREIGN PATENT DOCUMENTS

| | | |
|---|---|---|
| CN | 113444663 A | 9/2021 |
| CN | 113558244 A | 10/2021 |
| CN | 113969243 A | 1/2022 |
| WO | 9723619 A1 | 7/1997 |

OTHER PUBLICATIONS

GenCore., 2024, Sequence Alignment instant SEQ ID No. 1 and Lebeer's SEQ ID No. 4, pp. 1-2 (Year: 2024).*
Yilmaz et al., Microorganisms 2022, 10, 826, pp. 1-18 (Year: 2022).*

* cited by examiner

*Primary Examiner* — Lianko G Garyu
*Assistant Examiner* — Claudia Espinosa
(74) *Attorney, Agent, or Firm* — Analects Legal LLC

(57) ABSTRACT

The present disclosure relates to *Lactiplantibacillus plantarum* for degrading tannins and saponins, and a use thereof. The present disclosure is intended to solve the problem that the existing silage has a low utilization rate due to anti-nutritional factors such as tannins and saponins. The present disclosure provides *Lactiplantibacillus plantarum* P91 with an accession number of CGMCC No. 27567, which has acid resistance, a high growth rate, a strong carbon source-utilizing ability, and an excellent comprehensive acid-production ability, and can reduce a pH, well improve the palatability of silage, and reduce anti-nutritional factors in silage. Therefore, the present disclosure can effectively solve the problem that a silage raw material has a high content of anti-nutritional factors such as tannins and saponins, and overcome the adaptability problem of a *lactobacillus* to a raw material, thereby improving an activity of the *lactobacillus* and a quality of silage fermentation.

6 Claims, 4 Drawing Sheets

Specification includes a Sequence Listing.

LACTIPLANTIBACILLUS PLANTARUM FOR DEGRADING TANNINS AND SAPONINS, AND USE THEREOF

*LACTIPLANTIBACILLUS PLANTARUM FOR DEGRADING TANNINS AND SAPONINS, AND USE THEREOF*

CROSS-REFERENCE TO RELATED APPLICATIONS

This application claims priority to Chinese Patent Application No. 202310881780.4 filed on Jul. 18, 2023, the disclosure of which is hereby incorporated by reference in their entirety.

SEQUENCE LISTING

The instant application contains a Sequence Listing which has been submitted electronically in XML format and is hereby incorporated by reference in its entirety. Said XML copy, created on May 6, 2024, is named LACTIPLANTIBACILLUS PLANTARUM FOR DEGRADING TANNINS AND SAPONINS, AND USE THEREOF.xml and is 5,355 bytes in size. No new matter is hereby added.

TECHNICAL FIELD

The present disclosure relates to the technical field of microbial feeds, and in particular relates to *Lactiplantibacillus plantarum* for degrading tannins and saponins, and a use thereof.

BACKGROUND

Woody forages are rich in balanced amino acids and vitamins, and have a high crude protein content and a high nutrition value. Woody forages are a novel group of excellent protein feed resources. With the rapid development of the economy, there is a serious shortage of protein feeds in China, and in particular, *Medicago* and soy bean meals mainly rely on imports and have high costs. Therefore, woody forages are of great significance for alleviating the scarcity of protein feeds in China. However, tannins and saponins are major anti-nutritional factors in woody forages, and thus a too-high woody forage content in a diet for an animal will make the palatability and production performance of the animal reduced, and may even cause poisoning or death of the animal. Condensed tannins have extremely-strong astringency, and can affect the palatability of an animal by binding to glycoproteins in a mouth of the animal to produce bitter and astringent substances. Condensed tannins can be complexed with proteins (various digestive enzymes and nutrients) and minerals in an animal to produce complexes, which reduces the digestion and absorption of the animal for nutrients in a feed. Hydrolytic tannins can be digested and hydrolyzed to produce toxicity, thereby causing poisoning and even death to an animal. Saponins are slightly bitter and spicy, and may cause serious anorexia of an animal, thereby affecting the palatability of the animal. After being ingested, saponins produce complexes with nutrients such as proteins and minerals, which reduces the digestion and utilization of the nutrients in an animal.

Silage can not only preserve nutrients and active substances of a forage and improve the palatability and digestibility of a forage to smoothly provide a high-nutrient feed for overwintering animals, but also effectively degrade anti-nutritional factors and toxic and harmful substances in feed raw materials to improve a tolerance threshold of an animal to a feed. Currently, there are many reports on impacts of lactobacilli on nutritional values, active substances, and animal feeds. When a *lactobacillus* is used as an accelerating agent for silage fermentation, a type and quantity of the *lactobacillus* are key factors to determine whether anti-nutritional factors in silage can be degraded. The use of a *lactobacillus* for degrading anti-nutritional factors in silage has been rarely reported.

SUMMARY

In view of the above analysis, the present disclosure is intended to provide *Lactiplantibacillus plantarum* for degrading tannins and saponins, and a use thereof, and thus solve the problem that the silage in the prior art has a low utilization rate due to a high content of anti-nutritional factors such as tannins and saponins.

In a first aspect, the present disclosure provides *Lactiplantibacillus plantarum* P91 with an accession number of CGMCC No. 27567.

Further, the *Lactiplantibacillus plantarum* P91 includes 16S rDNA shown in SEQ ID NO: 1.

Further, the *Lactiplantibacillus plantarum* P91 is isolated from *Broussonetia papyrifera* silage.

In a second aspect, the present disclosure provides a silage additive including the *Lactiplantibacillus plantarum* P91 described above.

In a third aspect, the present disclosure provides silage including the *Lactiplantibacillus plantarum* P91 described above.

Further, the silage further includes *Caragana korshinskii* Kom. silage and/or *Moringa oleifera* Lam. silage.

In a fourth aspect, the present disclosure provides a preparation method of silage, including: mixing a silage raw material with the *Lactiplantibacillus plantarum* P91 described above, and allowing fermentation to obtain the silage.

Further, a mass ratio of the *Lactiplantibacillus plantarum* P91 to the silage raw material is $1.0\times10^5$ CFU/g to $2.0\times10^6$ CFU/g.

Further, the silage raw material includes *Caragana korshinskii* Kom, and/or *Moringa oleifera* Lam, and preferably, the silage raw material is *Caragana korshinskii* Kom.

In a fifth aspect, the present disclosure provides a use of the *Lactiplantibacillus plantarum* P91 described above in preparation of silage.

Compared with the prior art, the present disclosure can allow at least one of the following beneficial effects:

(1) The present disclosure provides *Lactiplantibacillus plantarum* P91. The *Lactiplantibacillus plantarum* P91 has acid resistance, a high growth rate, a strong carbon source-utilizing ability, and an excellent comprehensive acid-production ability, and can reduce anti-nutritional factors in silage. Therefore, the present disclosure can effectively solve the problem that a silage raw material has a high content of anti-nutritional factors such as tannins and saponins, well improve the palatability of silage, and overcome the adaptability problem of a *lactobacillus* to a raw material, thereby improving an activity of the *lactobacillus* and a quality of silage fermentation.

(2) The present disclosure provides silage in which *Lactiplantibacillus plantarum* P91 is introduced to improve a fermentation quality of the silage, which has advantages such as low cost, safety, reliability, and easy utilization.

The above technical solutions in the present disclosure can also be combined with each other to provide increased preferred combination solutions. Other features and advantages of the present disclosure will be described in the following description, and some of these will become apparent from the description or be understood by implementing the present disclosure. The objectives and other advantages of the present disclosure may be implemented or derived by those specifically indicated in the description and accompanying drawings.

BRIEF DESCRIPTION OF THE DRAWINGS

The accompanying drawings are provided merely to illustrate the specific embodiments, rather than to limit the present disclosure. The same reference numerals represent the same components throughout the accompanying drawings.

DETAILED DESCRIPTION OF THE EMBODIMENTS

Figure 1:
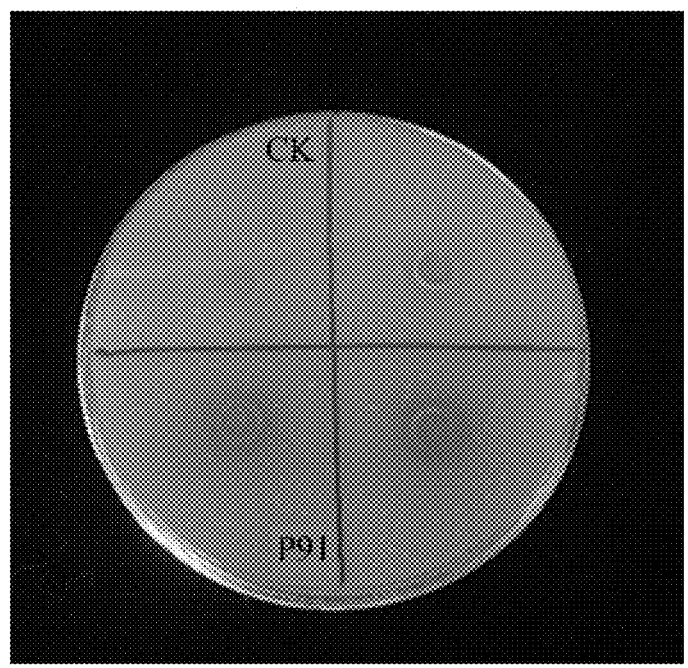
FIG. 1 shows discoloration circles of the *Lactiplantibacillus plantarum* P91 for degradation of tannins in the present disclosure.

Preferred embodiments of the present disclosure will be specifically described below with reference to the accompanying drawings. The accompanying drawings constitute a part of the present disclosure, and are used together with the embodiments of the present disclosure to explain the principles of the present disclosure rather than limit a scope of the present disclosure.

In a specific embodiment, the present disclosure provides *Lactiplantibacillus plantarum* P91, which was deposited in the China General Microbiological Culture Collection Center (CGMCC, Institute of Microbiology Chinese Academy of Sciences NO. 1 West Beichen Road, Chaoyang District, Beijing, China) on Jun. 6, 2023, with an accession number of CGMCC No. 27567.

In an embodiment, the *Lactiplantibacillus plantarum* P91 includes 16S rDNA shown in SEQ ID NO: 1.

In an embodiment, the *Lactiplantibacillus plantarum* P91 is isolated from *Broussonetia papyrifera* silage.

It should be noted that, before extraction and separation, the *Broussonetia papyrifera* silage is silage stored for 60 d, and as a preferred solution, *Broussonetia papyrifera* refers to hybrid *Broussonetia papyrifera*.

Specifically, a process of isolation and cultivation of the *Lactiplantibacillus plantarum* P91 includes:

a bag with the *Broussonetia papyrifera* silage is opened, the *Broussonetia papyrifera* silage is thoroughly mixed in a clean basin, an appropriate amount of the *Broussonetia papyrifera* silage is taken and mixed with 0.85% normal saline, and a resulting supernatant is collected, transferred to an MRS medium, and cultivated.

In an embodiment, a temperature for cultivation of the *Lactiplantibacillus plantarum* P91 is 15° C., to 45° C., and further can be 30° C., to 35° C., such as 20° C., 25° C., 27° C., 33° C., 37° C., or 40° C.

In an embodiment, after the *Lactiplantibacillus plantarum* P91 is cultivated in the MRS medium for 24 h, a pH value of the MRS medium is reduced to 3.5 to 4.0.

In an embodiment, a pH for cultivation of the *Lactiplantibacillus plantarum* P91 is 4.5 to 7.0.

In an embodiment, a salt concentration for cultivation of the *Lactiplantibacillus plantarum* P91 is 3.0% to 6.5% NaCl.

It should be noted that the biological characteristics of the *Lactiplantibacillus plantarum* P91 in the present disclosure is a Gram-positive coccus allowing glucose homolactic fermentation. The *Lactiplantibacillus plantarum* P91 can grow normally at a pH of 4.5, indicating strong acid resistance. The *Lactiplantibacillus plantarum* P91 can grow well in environments with salt concentrations of 3.0% and 6.5%, respectively, indicating excellent salt resistance. After the *Lactiplantibacillus plantarum* P91 is cultivated in an MRS liquid medium at 37° C. for 48 h, OD600 nm is 1.6218, indicating a high growth rate. A test is conducted at 30° C., with Profile Index (API 50 CH, blomerieux, France) test strips. In addition to carbon sources that can be utilized by the *Lactiplantibacillus plantarum* P91, the *Lactiplantibacillus plantarum* P87 can well utilize D-fructose and dulcitol, as shown in Tables 6 and 8. It indicates that there is a difference in the utilization of carbon sources between the two strains.

In another specific embodiment, the present disclosure provides a silage additive including the *Lactiplantibacillus plantarum* P91 described above.

Further, the additive is a hybrid *Broussonetia papyrifera* silage additive.

In another specific embodiment, the present disclosure provides silage including the *Lactiplantibacillus plantarum* P91 described above.

In an embodiment, the silage further includes *Caragana korshinskii* Kom. silage and/or *Moringa oleifera* Lam. silage.

Further, the silage further includes *Caragana korshinskii* Kom. silage and *Moringa oleifera* Lam. silage.

In another specific embodiment, the present disclosure provides a preparation method of silage, including: a silage raw material is mixed with the *Lactiplantibacillus plantarum* P91 described above, and fermentation is allowed to obtain the silage.

In an embodiment, a mass ratio of the *Lactiplantibacillus plantarum* P91 to the silage raw material is $1.0 \times 10^5$ CFU/g to $2.0 \times 10^6$ CFU/g, for example, the mass ratio is $2.0 \times 10^5$ CFU/g, $5.0 \times 10^5$ CFU/g, $8.0 \times 10^5$ CFU/g, $1.0 \times 10^6$ CFU/g, or $1.5 \times 10^6$ CFU/g.

Specifically, in an embodiment, the present disclosure provides a preparation method of silage, including the following steps:

S1: a raw material is chopped and thoroughly mixed;

S2: the *Lactiplantibacillus plantarum* P91 is added to the raw material at a level of $1.0 \times 10^6$ CFU/g or more; and S3: a resulting feed system is vacuum-sealed and stored.

In an embodiment, in the S1, the raw material includes *Caragana korshinskii* Kom, and *Moringa oleifera* Lam., and further, *Caragana korshinskii* Kom, and *Moringa oleifera* Lam. manually mowed are chopped to 2 cm to 3 cm.

In an embodiment, in the S3, a vacuum-sealed feed system is stored at 20° C., to 25° C., and after the vacuum-sealed feed system is stored for 90 d, a pH of the vacuum-sealed feed system is reduced to 3.92.

In another specific embodiment, the present disclosure provides a use of the *Lactiplantibacillus plantarum* P91 in preparation of silage.

It should be noted that the *Lactiplantibacillus plantarum* P91 in the present disclosure has acid resistance, a high growth rate, a strong carbon source-utilizing ability, and an excellent comprehensive acid-production ability, and can reduce anti-nutritional factors in silage. Therefore, the present disclosure can effectively solve the problem that a silage raw material has a high content of anti-nutritional factors such as tannins and saponins, well improve the palatability of silage, and overcome the adaptability problem of a *lactobacillus* to a raw material, thereby improving an activity of the *lactobacillus* and a quality of silage fermentation.

Through the use of a plant epiphytic *lactobacillus* in silage, the present disclosure overcomes the problem that a *lactobacillus* exhibits low adaptability to a raw material during silage, and reduces the contents of tannins and saponins.

In the silage of the present disclosure, a *lactobacillus* is used to improve a fermentation quality of silage and reduce anti-nutritional factors in silage, which has advantages such as low cost, safety, reliability, and easy utilization.

The *Lactiplantibacillus plantarum* P91 and silage in an embodiment of the present disclosure are further described below in conjunction with the accompanying drawings and specific examples.

The *Caragana korshinskii* Kom. material used comes from the Inner Mongolia Jinji Biotechnology Co., Ltd., Chifeng City, Inner Mongolia Autonomous Region (North Latitude: 43.97°, East Longitude: 119.38°, altitude: 687 m, average annual temperature: 5.8° C., and average annual precipitation: 314.5 mm). The *Moringa oleifera* Lam. material comes from the experimental base of the South China Agricultural University, Guangzhou City, Guangdong Province (North Latitude: 23.14°, East Longitude: 113.32°, altitude: 11 m, average annual temperature: 22.2° C., and average annual precipitation: 1,632 mm to 2,899 mm).

The *Broussonetia papyrifera* silage raw material comes from the Rongcheng Gouyang Modern Agriculture (Chongqing) Co., Ltd., Rongchang District, Chongqing: North Latitude: 29.42°, East Longitude: 105.61°, altitude: 380 m, relative humidity: 76%, average annual temperature: 17.8° C., and average annual precipitation: 1,099 mm. A specific preparation method of the *Broussonetia papyrifera* silage is as follows: the *Broussonetia papyrifera* silage raw material is chopped to 2 cm to 3 cm, an appropriate amount of a chopped raw material is uniformly taken and placed on a clean plastic sheet, and about 500 g of a fresh *Broussonetia papyrifera* sample is taken and placed in a double-sided twill silage bag (28 cm×35 cm), and stored at room temperature (25±2° C.).

An MRS liquid medium used for the isolation and cultivation of the *Lactiplantibacillus plantarum* P91 and the determination of physiological and biochemical indexes such as growth rate and acid-producing rate includes the components shown in Table 1 below:

TABLE 1

Components of the MRS liquid medium

| Component | Content (g) |
| --- | --- |
| Peptone | 10.0 |
| Beef powder | 5.0 |
| Yeast powder | 4.0 |
| Glucose | 20.0 |
| Tween 80 | 1 mL |
| Triammonium citrate | 2.0 |
| Sodium acetate | 5.0 |

TABLE 1-continued

Components of the MRS liquid medium

| Component | Content (g) |
| --- | --- |
| Magnesium sulfate | 0.2 |
| Manganese sulfate | 0.05 |
| Dipotassium phosphate | 2.0 |
| Distilled water | 1000 mL |

An MRS solid medium is obtained by adding 15 g of agar on the basis of the MRS liquid medium. The above media are sterilized at 121° C., in an autoclave for 15 min.

Example 1

Isolation and Primary Screening of Bacteria for Degrading Tannins and Saponins
1. Isolation and Purification of Strains 20 g of *Broussonetia papyrifera* silage (which had been stored for 60 d) was taken and placed in a clean sealed bag filled with 180 mL of sterile normal saline (0.85% NaCl solution), then the sealed bag was fully shaken and placed in a 4° C. refrigerator to allow leaching for 4 h, and then 1 mL of a resulting supernatant (which was denoted as a $10^{-1}$ concentration gradient) was taken and 10-fold diluted serially to a $10^{-2}$ concentration gradient, a $10^{-3}$ concentration gradient, and a $10^{-4}$ concentration gradient. 100 μL of a dilution at each gradient was spread on an MRS agar plate and cultivated in a 37° C., incubator for 48 h. According to the morphologies, colors, and sizes of single colonies, typical colonies were selected and purified at least twice by a plate streaking method until obtaining single colonies of lactobacilli. A *lactobacillus* was transferred to a 10% dimethyl sulfoxide-containing NB nutrient medium by a colony enrichment method, and stored in a −80° C. refrigerator. A composition of the MRS solid medium was as above.

2. Primary Screening of Lactobacilli Capable of Degrading Both Tannins and Saponins A tannin-containing solid screening medium was equally divided into four parts, and a sterile Oxford cup was placed by sterile forceps on a surface of the medium at a corresponding position and pressed gently. An activated pure *lactobacillus* solution (100 μL) was taken and spot-inoculated in the Oxford cup, and an inoculated medium was slowly placed in a 30° C., incubator and cultivated for 24 h to 48 h. A growth status of a colony and a size of a discoloration circle around a colony were observed. Colonies with transparent circles were preliminarily regarded as having an ability to degrade tannins, and this strain was selected and subsequently subjected to primary saponin-degradation screening by measuring a tannase-producing activity of this strain. Components of the medium for primary screening of tannin-degrading lactobacilli are shown in Table 2 below.

TABLE 2

Components of the medium for primary screening of tannin-degrading lactobacilli

| Component | Percentage content (w/v) |
| --- | --- |
| Tannic acid | 1.00 |
| Agar | 2.50 |
| NaNO$_3$ | 0.30 |
| K$_2$HPO$_4$ | 0.10 |
| MgSO$_4$ · 7H$_2$O | 0.05 |

TABLE 2-continued

Components of the medium for primary screening of tannin-degrading lactobacilli

| Component | Percentage content (w/v) |
|---|---|
| KCl | 0.05 |
| $FeSO_4 \cdot 7H_2O$ | 0.001 |
| Bromophenol blue | 0.004 |
| pH | 5.0 |

100 μL of a tannin-degrading pure bacterial solution screened above was added to a saponin-containing solid screening medium, and uniformly coated on a surface of the medium, and cultivated at 30° C. for 48 h. If colonies grew, it was preliminarily determined that a corresponding strain had an ability to utilize saponins, and the strain was stored and subjected to subsequent secondary screening. Components of the medium for preliminary screening of saponin-degrading lactobacilli are shown in Table 3 below.

TABLE 3

Components of the medium for primary screening of saponin-degrading lactobacilli

| Component | Thousandth content (w/v) |
|---|---|
| Saponin | 10.00 |
| Agar | 20.00 |
| $(NH_4)_2SO_4$ | 1.00 |
| $K_2HPO_4$ | 1.50 |
| $KH_2PO_4$ | 0.50 |
| NaCl | 1.00 |
| $MgSO_4$ | 0.20 |
| $FeSO_4$ | 0.05 |
| pH | 7.00 |

Secondary Screening of Bacteria Capable of Degrading Both Tannins and Saponins

Determination of tannase: A bacterial solution capable of degrading both tannins and saponins that was primarily screened above and activated for 24 h was inoculated into a tannase-production medium (a composition of the tannase-production medium was shown in Table 4) and cultivated in a constant-temperature shaker at 150 rpm and 30° C. for 24 h, and a resulting bacterial solution was centrifuged at 10,000 rpm and 4° C. for 10 min to obtain a supernatant, which was a crude tannase solution. A propyl gallate (PG) solution required by the experiment and a crude tannase solution to be tested each were incubated in a 30° C., water bath for 5 min to 10 min. 0.25 mL of the PG solution was added to each test tube: 0.25 mL of a crude tannase solution was added to an experimental tube, and 0.25 mL of a citric acid buffer was added to a blank tube; each test tube was thoroughly vortexed and then incubated in a 30° C., water bath for 5 min; then 0.3 mL of a rhodanine methanol solution was added to each tube, and each test tube was incubated for 5 min; then 0.4 mL of a KOH solution was added to each test tube: 3.8 mL of distilled water was added to each test tube to dilute a reaction system, and a diluted reaction system was incubated at 30° C. for 5 min to 10 min; and with distilled water as a blank, an appropriate amount of a final reaction solution was taken and tested by a microplate reader for absorbance at 520 nm, and a tannase activity was calculated. The tannase activity was calculated as follows: $A_{520}=(A_{test}-A_{blank})-(A_{control}-A_{blank})$. With gallic acid as a standard, a standard curve was plotted, where a standard equation was $y=0.001x+0.051$ and $R^2=0.9917$. A tannase activity was 183.47 μmol/min·mL.

TABLE 4

Tannase-production medium

| Component | Percentage content (w/v) |
|---|---|
| Tannic acid | 2.00 |
| Sucrose | 1.00 |
| $NaNO_3$ | 0.30 |
| $K_2HPO_4$ | 0.10 |
| KCl | 0.05 |
| $MgSO_4 \cdot 7H_2O$ | 0.05 |

Determination of a degradation rate of saponins: The degradation rate of saponins was used as an index for the secondary screening. Preparation of a crude saponin fermentation broth: A strain to be tested was inoculated into a saponin primary screening medium without agar, and fermentation was conducted in a shaking flask for 24 h (until the medium was turbid); a resulting bacterial solution was frozen-centrifuged at 4° C. (8.000 rpm. 10 min) to obtain a supernatant: the bacterial precipitate was washed 3 times with sterile water: the supernatant was collected and diluted to 250 mL to obtain the crude saponin fermentation broth; and 5 mL of the crude saponin fermentation broth was diluted to 100 mL, and a diluted crude saponin fermentation broth was stored in a refrigerator at 4° C. for later use. 0.5 mL of the diluted crude saponin fermentation broth was taken and tested for absorbance at 550 nm, with distilled water as a blank. Degradation rate of saponins (W)=1-C/Co×100%, where W represents a degradation rate of saponins. C represents a content of saponins after fermentation, and Co represents a content of saponins before fermentation. A degradation rate of saponins by degradation bacteria was 51.52%.

A strain with a tannase activity of 183.47 μmol/min·mL and a saponin degradation rate of 51.52% was selected as a degradation strain, and the degradation strain was subjected to the following morphological identification and physiological and biochemical tests.

Morphological Identification of the Degradation Strain

Processes of Gram staining. cell shape observation, and a catalase experiment were as follows:

Gram staining: A specified amount of water was picked to a center of a glass slide, then a small amount of the strain was picked with an inoculation loop and thoroughly mixed with water droplets on the glass slide, and a resulting mixture was coated to form a thin bacterial film and then naturally dried. The glass slide was fixed upwards above a slight fire, initially stained with crystal violet for 1 min, and then rinsed with water thoroughly (which should be gentle to prevent a water flow from directly impacting bacterial blocks). An iodine solution was added dropwise to the glass slide to allow mordant-staining for 1 min to 2 min, and then the glass slide was decolorized with 95% ethanol and washed with water. The glass slide was counter-stained with safranin for 1 min to 2 min. then washed with water, naturally dried, and then observed under a 1.000-amplification oil immersion lens. Bacteria stained blue-purple were Gram-positive bacteria, and bacteria stained red were Gram-negative bacteria.

Catalase experiment: A 3% (volume fraction) hydrogen peroxide solution was pipetted with a pipette tip and added to a plate, a small amount of bacteria was picked with an inoculation loop and thoroughly mixed with the hydrogen peroxide solution, and 2 min to 3 min later, the plate was observed. If it was observed that there were bubbles, the bacteria were positive, and if it was observed that there were no bubbles, the bacteria were negative.

Physiological and Biochemical Tests of the Degradation Strain

The degradation strain was tested according to growth temperatures (4° C. 15° C. 30° C. 35° C., and 45° C.) and growth pH values (3.0, 3.5, 4.0, 4.5, and 9.0), and a process was as follows:

Determination and screening of acid productions and growth rates of the degradation strain: An isolated and purified strain was inoculated into 3 mL of an MRS liquid medium and cultivated overnight on a shaker at 30° C., and 250 rpm for about 14 h to 16 h. A resulting bacterial solution was inoculated at an inoculum size of 1% (V/V) into 3 mL of a fresh MRS liquid medium and cultivated on a shaker at 30° C., and 250 rpm, and at 0 h, 2 h, 4 h, 6 h, 8 h, 10 h, 12 h, 14 h, 16 h, 18 h, 20 h, 22 h, 24 h, and 48 h after the inoculation, a pH value of the MRS liquid medium was measured and an absorbance value was measured at a wavelength of 600 nm. 3 replicates needed to be set for each strain at each time point, and test tubes for cultivating bacteria needed to be of a same specification.

Temperature resistance test: A strain was inoculated at an inoculum size of 1% (V/V) into a fresh MRS liquid medium, and cultivated for 2 d at constant temperatures of 4° C., 15° C., 30° C., 35° C., and 45° C.

pH resistance test: A strain was inoculated at an inoculum size of 1% (V/V) into MRS liquid media with pH values of 3.0, 3.5, 4.0, 4.5, and 9.0, respectively, and cultivated for 2 d at 30° C. (a pH was adjusted with 2.0 M NaOH or 1.0 M HCl).

Salt resistance: The degradation strain was inoculated into MRS liquid media with NaCl contents of 3% and 6.5%, respectively, and then cultivated in a 30° C., incubator for 2 d, and then a growth status of the degradation strain was observed.

According to results of the above tests, a temperature for cultivation of the degradation strain is 15° C., to 45° C., a pH for cultivation of the degradation strain is 4.5 to 7.0, and a salt concentration for cultivation of the degradation strain is 3.0% to 6.5% NaCl. The degradation strain can grow normally under the above conditions.

Figure 3:
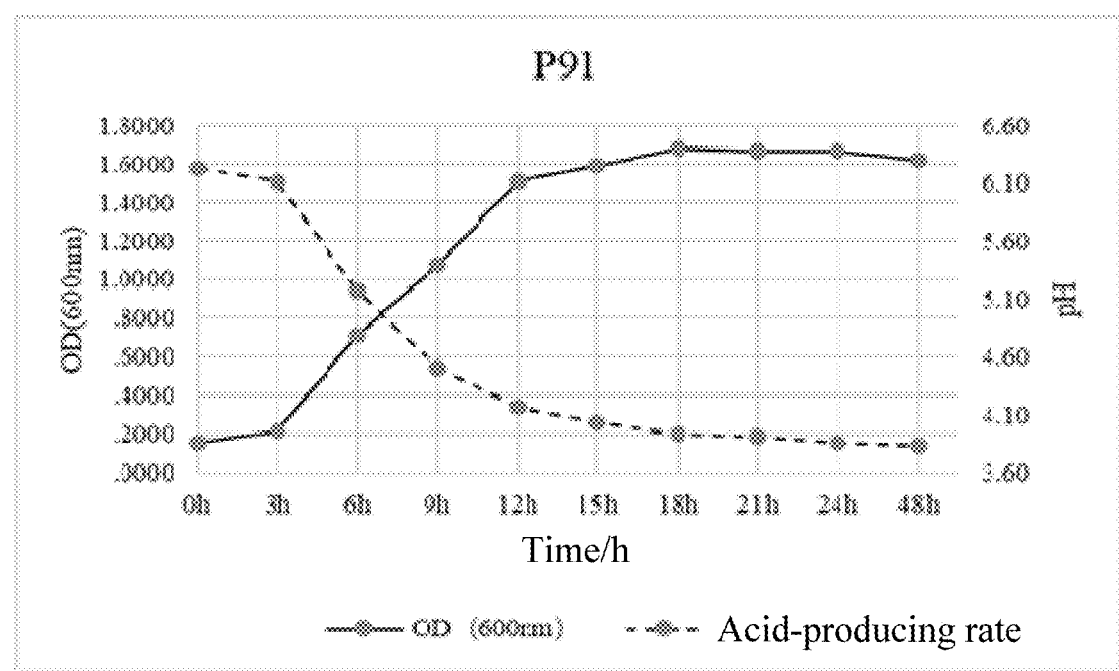
FIG. 3 shows acid-producing and growth rates of the *Lactiplantibacillus plantarum* P91 prepared in Example 1 of the present disclosure.

The morphology and physiological and biochemical characteristics of the degradation strain are shown in Table 5, and the acid-producing and growth rates of the degradation strain are shown in FIG. 3.

TABLE 5

Morphology and physiological and biochemical characteristics of the degradation strain

| Strain | Degradation strain |
|---|---|
| Source | *Broussonetia papyrifera* silage |
| Morphology | Rod-shaped |
| Gram staining | + |
| Catalase | − |
| Fermentation type | Homolactic |
| 4° C. | − |
| 15° C. | ++ |
| 35° C. | +++ |
| 45° C. | ++ |
| 3.0 | − |
| 3.5 | − |
| 4.0 | − |
| 4.5 | ++ |
| 5.0 | + |
| 5.5 | ++ |
| 6.0 | +++ |
| 7.0 | +++ |
| 3% NaCl | +++ |
| 6.5% NaCl | ++ |

Notes:
In Table 5, the "−", "+", "++", and "+++" in the resistance tests have the following meanings: −: $OD_{600\,nm} < 0.5$; +: $0.5 \leq OD_{600\,nm} < 1.0$; ++: $1.0 \leq OD_{600\,nm} < 1.5$; and +++: $1.5 \leq OD_{600\,nm}$.

TABLE 6

Carbon sources utilized by the degradation strain

| Item | | Degradation strain | Item | | Degradation strain |
|---|---|---|---|---|---|
| CK | Control | − | ESC | Esculin ferric citrate | + |
| GLY | Glycerol | W | SAL | Salicin | + |
| EERY | Erythritol | − | CEL | D-cellobiose | + |
| DARA | D-arabinose | W | MAL | D-maltose | + |
| LARA | L-arabinose | + | LAC | D-lactose | + |
| RIB | D-ribose | + | MEL | D-melibiose | + |
| DXYL | D-xylose | + | SAC | D-sucrose | + |
| LXYL | L-xylose | W | TRE | D-trehalose | + |
| ADO | D-adonitol | W | INU | Inulin | + |
| MDX | Methyl-β-D xylopyranoside | W | MLZ | D-melezitose | + |
| GAL | D-galactose | + | RAF | D-raffinose | + |
| GLU | D-glucose | + | AMD | Starch | W |
| FRU | D-fructose | + | GLYG | Glycogen | W |
| MNE | D-mannose | + | XLT | Xylitol | W |
| SBE | L-sorbose | W | GEN | D-gentiobiose | + |
| RHA | L-rhamnose | W | TUR | D-Turanose | + |
| DUL | Dulcitol | W | LYX | D-lyxose | W |
| INO | Inositol | W | TAG | D-tagatose | + |
| MAN | Mannitol | + | DFUC | D-fucose | W |
| SOR | Sorbitol | + | LFUC | L-fucose | W |
| MDM | Methyl-α-D-mannopyranoside | + | DARL | D-arbaitol | W |

TABLE 6-continued

Carbon sources utilized by the degradation strain

| Item | | Degradation strain | Item | | Degradation strain |
|---|---|---|---|---|---|
| MDG | Methyl-α-D-glucopyranoside | + | LARL | L-arbaitol | W |
| NAG | N-Acetyl glucosamine | + | GNT | Potassium gluconate | + |
| AMY | Amygdalin | + | 2KG | 2-Keto-potassium gluconate | − |
| ARB | Arbulin | + | 5KG | 5-Keto-potassium gluconate | W |

Notes:
"w", "+", and "−" in Table 6 have the following meanings: w: weakly positive, +: positive, and −: negative.

The results in Tables 5 and 6 show that the degradation strain is a Gram-positive bacillus allowing homolactic fermentation, and has strong acid and salt resistance, a high growth rate, and a strong comprehensive acid-production ability.

Comparative Example 1

A bag with the *Broussonetia papyrifera* silage was opened, the *Broussonetia papyrifera* silage was thoroughly mixed in a clean basin, 20 g of the *Broussonetia papyrifera* silage (which had been stored for 60 d) was taken and mixed with 180 mL of 0.85% normal saline (NaCl), a resulting mixture was placed in a 4° C. refrigerator to allow leaching for 4 h, and then a resulting supernatant was collected and 10-fold diluted serially to a $10^4$ concentration gradient and a $10^{-5}$ concentration gradient. 100 μL of a dilution at each gradient was coated on a plate with an MRS medium and cultivated in a 30° C., incubator for 48 h. After bacterial colonies grew, bacterial colonies were picked and separated through at least 2 times of plate streaking to obtain single colonies A, and the single colonies A were stored with dimethyl sulfoxide in a −80° C. refrigerator.

Strains of the single colonies A were subjected to primary screening, secondary screening, identification, and tests according to the methods in Example 1 to finally obtain a strain B capable of degrading both tannins and saponins. Relevant results of the strain B are shown in Tables 7 and 8.

TABLE 7

Morphology and physiological and biochemical characteristics of the strain B

| Strain | Strain B |
|---|---|
| Source | *Broussonetia papyrifera* silage |
| Morphology | Rod-shaped |
| Gram staining | + |
| Catalase | − |
| Fermentation type | Heterolactic |
| 4° C. | − |
| 15° C. | ++ |
| 35° C. | +++ |
| 45° C. | + |
| 3.0 | − |
| 3.5 | − |
| 4.0 | + |
| 4.5 | ++ |
| 5.0 | ++ |
| 5.5 | +++ |
| 6.0 | + |
| 7.0 | +++ |
| 3% NaCl | +++ |
| 6.5% NaCl | ++ |

Notes:
In Table 7, the "−", "+", "++", and "+++" in the resistance tests have the following meanings: −: $OD_{600\ nm} < 0.5$; +: $0.5 \leq OD_{600\ nm} < 1.0$; ++: $1.0 \leq OD_{600\ nm} < 1.5$; and +++: $1.5 \leq OD_{600\ nm}$.

TABLE 8

Carbon sources utilized by the strain B

| Item | | Strain B | Item | | Strain B |
|---|---|---|---|---|---|
| CK | Control | − | ESC | Esculin ferric citrate | + |
| GLY | Glycerol | − | SAL | Salicin | + |
| EERY | Erythritol | − | CEL | D-cellobiose | + |
| DARA | D-arabinose | − | MAL | D-maltose | + |
| LARA | L-arabinose | + | LAC | D-lactose | + |
| RIB | D-ribose | + | MEL | D-melibiose | + |
| DXYL | D-xylose | W | SAC | D-sucrose | + |
| LXYL | L-xylose | − | TRE | D-trehalose | + |
| ADO | D-adonitol 1 | − | INU | Inulin | + |
| MDX | Methyl-β-D xylopyranoside | − | MLZ | D-melezitose | + |
| GAL | D-galactose | + | RAF | D-raffinose | + |
| GLU | D-glucose | + | AMD | Starch | W |
| FRU | D-fructose | + | GLYG | Glycogen | W |
| MNE | D-mannose | + | XLT | Xylitol | W |
| SBE | L-sorbose | W | GEN | D-gentiobiose | + |
| RHA | L-rhamnose | + | TUR | D-Turanose | + |
| DUL | Dulcitol | + | LYX | D-lyxose | W |
| INO | Inositol | W | TAG | D-tagatose | W |
| MAN | Mannitol | + | DFUC | D-fucose | W |
| SOR | Sorbitol | + | LFUC | L-fucose | − |
| MDM | Methyl-α-D-mannopyranoside | + | DARL | D-arbaitol | W |
| MDG | Methyl-α-D-glucopyranoside | + | LARL | L-arbaitol | W |
| NAG | N-Acetyl glucosamine | + | GNT | Potassium gluconate | + |
| AMY | Amygdalin | + | 2KG | 2-Keto-potassium gluconate | − |
| ARB | Arbulin | + | 5KG | 5-Keto-potassium gluconate | W |

Notes:
"w", "+", and "−" in Table 8 have the following meanings: w: weakly positive, +: positive, and −: negative.

Figure 4:
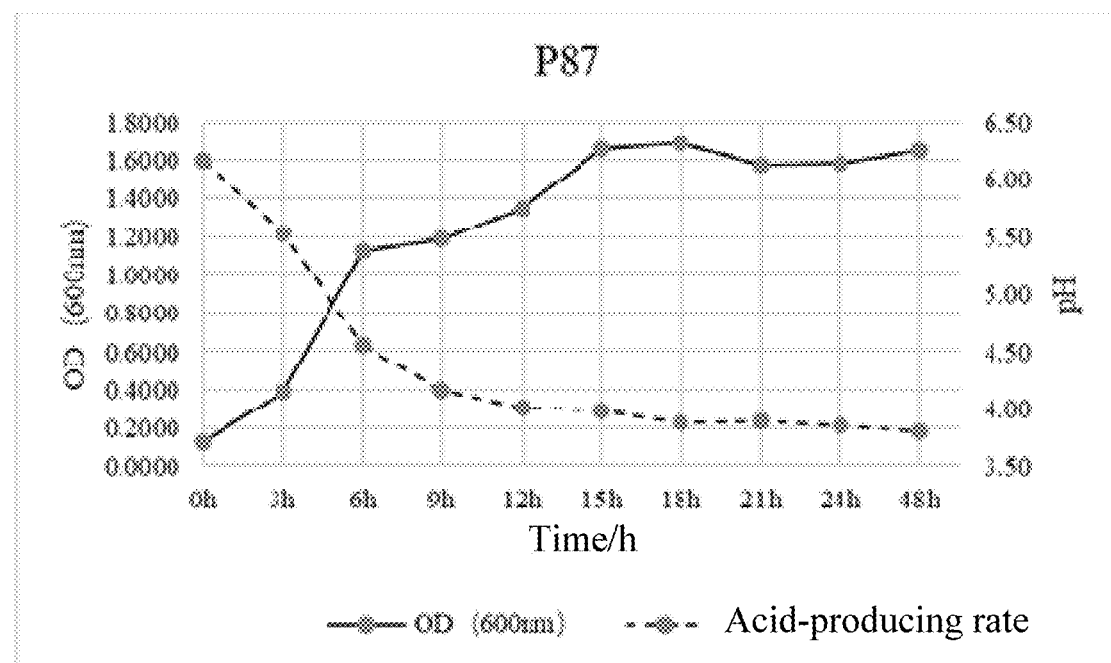
FIG. 4 shows acid-producing and growth rates of the *Lactiplantibacillus plantarum* P87 prepared in Comparative Example 1 of the present disclosure.

The results in Tables 7 and 8 show that the strain B is a Gram-positive coccus allowing heterolactic fermentation, and has strong salt resistance, a high growth rate, and a strong comprehensive acid-production ability. Acid-production and growth rates of the strain B are shown in FIG. 4. The Degradation Strain Obtained in Example 1 and the Strain B Obtained in Comparative Example 1 were Subjected to Homology Analysis with a 16S rDNA Gene A strain was cultivated overnight at 35° C., in 5 mL of an MRS medium, a resulting bacterial solution was then transferred to a 1.5 mL centrifuge tube and centrifuged at 10,000 rpm/min for 3 min to 5 min to obtain a bacterial pellet, the bacterial pellet was washed twice with TE 0.1 (10 mmol/L Tris-HCL, 0.1 mmol/L EDTA, pH 8.0) and then subjected to DNA extraction with a TIANamp Bacteria DNA Kit (TIANGEN BIOTECH CO., LTD., Beijing, China), and the absorbance OD600 nm was detected.

Then PCR amplification was conducted. Amplification primers for 16S rDNA were 27f and 1492r (Monis et al., 2005), and a PCR procedure was as follows: 95° C. (5 min), −94° C. (30 s), −55° C. (1 min), −72° C. (1.5 min), and −72° C. (10 min), where there were 30 cycles of 94° C. (30 s), −55° C. (1 min), and −72° C. (1.5 min). Amplification products were sent to Shenzhen Huada gene Technology Co., Ltd. (China) for sequencing. Sequencing results were subjected to alignment in the gene bank of NCBI to find out a standard *Lactiplantibacillus plantarum* strain with a close relationship to a corresponding strain. Through the DNAman software, a screened strain was subjected to similarity analysis with a standard strain in terms of a partial sequence (about 1,400 bp to 1,500 bp) of 16S rDNA (16S rDNA of the degradation strain was shown in SEQ ID NO: 1, and 16S rDNA of the strain B was shown in SEQ ID NO: 2), and the similarity between the degradation strain or the strain B and *Lactiplantibacillus plantarum* was more than 99%. Thus, in combination with physiological and biochemical indexes, it was determined that the degradation strain and the strain B both were the same species as *Lactiplantibacillus plantarum*. In the present disclosure, the degradation strain is the *Lactiplantibacillus plantarum* P91 of the present disclosure, and the strain B is the *Lactiplantibacillus plantarum* P87 of the present disclosure.

Figure 2:
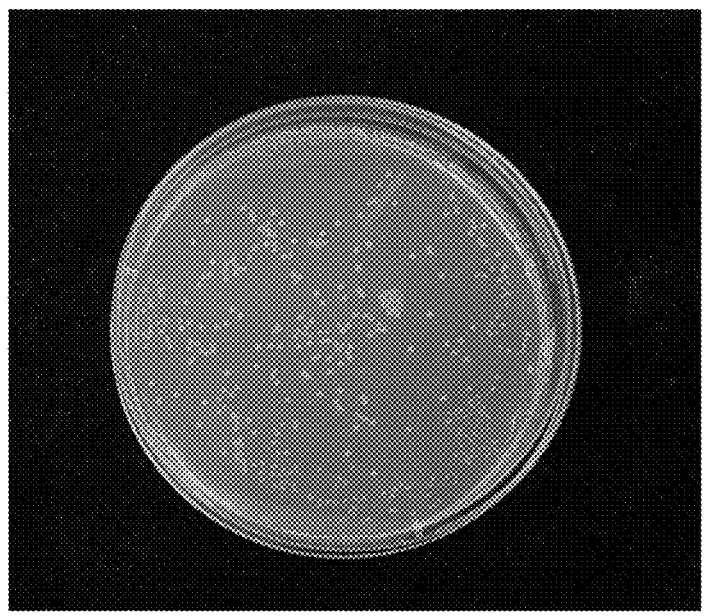
FIG. 2 shows a growth status of colonies of the *Lactiplantibacillus plantarum* P91 with saponins as an only carbon source in the present disclosure.

Discoloration circles of the *Lactiplantibacillus plantarum* P91 for degradation of tannins are shown in FIG. 1, and colonies of the *Lactiplantibacillus plantarum* P91 with saponins as an only carbon source are shown in FIG. 2.

Use Example

1. Preparation of Silage

*Caragana korshinskii* Kom. from the Inner Mongolia Jinji Biotechnology Co., Ltd., Chifeng City, Inner Mongolia Autonomous Region and *Moringa oleifera* Lam. from the experimental base of the South China Agricultural University. Guangzhou City. Guangdong Province were cut to 2 cm to 3 cm and thoroughly mixed to obtain a mixed material, and the *Lactiplantibacillus plantarum* P91 (P91 treatment group) in Example 1 and the *Lactiplantibacillus plantarum* P87 (P87 treatment group) in Comparative Example 1 each were inoculated into the mixed material at an amount of about $1\times10^6$ CFU/g. A resulting mixture in each treatment group was thoroughly mixed and then packed in three 28 cm×35 cm polyethylene silage bags with about 500 g of the mixture in each bag, and the polyethylene silage bags were vacuumed by a vacuum sealing machine for sealing and then stored at a temperature of 20° C., to 25° C., to allow fermentation for 90 d.

2. Tests of *Caragana korshinskii* Kom, and *Moringa oleifera* Lam. Raw Materials and Silage Samples were taken to analyze anti-nutritional components in the *Caragana korshinskii* Kom, and *Moringa oleifera* Lam. raw materials and the silage obtained after a silage treatment with an additive for 90 d. Specific results are shown in Tables 9 and 10. Test processes are as follows:

Dry matter (DM) contents in the raw materials and the silage each were determined by a lyophilization method as follows: a sample was thoroughly mixed and then lyophilized in a lyophilizer for 5 d or more until a mass of the sample was constant, and a dry matter content in the sample was determined. An oven-dried sample was crushed by a plant crusher. sieved through a 40-mesh sieve, and then tested for anti-nutritional components.

A determination method of tannins was obtained through an appropriate adjustment with reference to Zhang Yingchao (2019. Screening of Excellent Lactobacilli and Research on Action Mechanisms of Lactobacilli in Typical Woody Forage Silage). 0.2 g of a lyophilized and crushed sample was weighed and added to a 25 mL round-bottom centrifuge tube. 5 mL of 70% acetone was added to the round-bottom centrifuge tube to obtain a first mixture, and the first mixture was ultrasonically-treated at room temperature for 20 min and then centrifuged at 4° C., and 8.000 rpm for 10 min. The above process was repeated once, and a final extraction system was diluted to 25 mL and stored in an ice bath to obtain an extraction solution. 0.1 mL of the extraction solution was added to a 15 mL centrifuge tube, distilled water was added to the centrifuge tube to allow a total volume of 1.0 mL, and then 0.5 mL of a Folin reagent and 2.5 mL of a 20% sodium carbonate reagent were added to obtain a second mixture; and the second mixture was thoroughly mixed and shaken at room temperature for 40 min to obtain a reaction solution, an appropriate amount of the reaction solution was taken and tested by a microplate reader for absorbance at 720 nm, and a total phenol content was calculated. With gallic acid as a standard, a standard curve was plotted. 0.1 g of insoluble polyvinylpyrrolidone was taken and added to a 10 mL centrifuge tube. 1 mL of distilled water and the extracting solution were added to the centrifuge tube, and the centrifuge tube was thoroughly vortexed, allowed to stand at 4° C. for 15 min, and then centrifuged at 8.000 rpm for 10 min to obtain a supernatant: 0.1 mL of the supernatant was collected in a test tube. 0.9 mL of distilled water was added to the test tube, and then 0.5 mL of a Folin reagent and 2.5 mL of a 20% sodium carbonate reagent were added successively to obtain a mixture; and the mixture was thoroughly mixed and shaken at room temperature for 40 min to obtain a reaction solution, an appropriate amount of the reaction solution was taken and tested by a microplate reader for absorbance at 720 nm, and a total phenol content was calculated. With gallic acid as a standard, a standard curve was plotted. A hydrolytic tannin content was a difference between a total phenol content and a simple phenol content. A condensed tannin content was determined by a Vanilli-HCl method. 0.1 g of a lyophilized and crushed sample was accurately weighed and added to a 15 mL round-bottom centrifuge tube. 5 mL of a 1% hydrochloride methanol solution was added to the centrifuge tube, and the centrifuge tube was shaken at room temperature for 20 h and then centrifuged at 8.000 rpm for 10 min to obtain a supernatant, and the supernatant was collected and diluted to 5 mL to obtain a condensed tannin leaching liquor. 1 mL of the condensed tannin leaching liquor was taken and added to a test tube. 5 mL of a vanillin chromogenic solution was added to the test tube, and the test tube was vortexed for thorough mixing and then allowed to stand at room temperature for 20 min to obtain a reaction solution. An appropriate amount of the reaction solution was taken and tested by a microplate reader for absorbance at 495 nm, and a condensed tannin content was calculated. With catechin as a standard, a standard curve was plotted. A sum of a hydrolytic tannin content and a condensed tannin content was a total tannin content.

A total saponin content was determined with reference to Zhang Jiming (2015. Study on Total Saponin Contents in *Medicago sativa* L. of Different Varieties Treated with Additive at Mowing Stage) as follows: 0.5 g of a lyophilized and crushed sample was accurately weighed and placed in a 50 mL centrifuge tube. 15 mL of 70% ethanol was added to the centrifuge tube to obtain a first mixture, the first mixture was ultrasonically treated at room temperature for 15 min, then incubated in a 75° C. water bath for 15 min, and centrifuged at 8.000 rpm for 10 min to obtain a supernatant, and the supernatant was diluted to 25 mL to obtain a total saponin leaching liquor. 0.1 mL of the total saponin leaching liquor was taken and added to a glass test tube, and then the glass test tube was placed in an 80° C., water bath for evaporation to dryness, and cooled; then 0.2 mL of a 5% vanillin-glacial acetic acid solution and 0.8 mL of perchloric acid were added at one time to the glass test tube, and the glass test tube was vortexed for thorough mixing, heated in a 75° C., water bath for 20 min, and then quickly cooled in an ice bath; 5 mL of glacial acetic acid was added to the glass test tube, and the glass test tube was vortexed and allowed to stand for 10 min to obtain a reaction solution; and an appropriate amount of the reaction solution was taken and tested by a microplate reader for absorbance at 545 nm, and a total saponin content was calculated. With oleanolic acid as a standard, a standard curve was plotted.

Contents of hydrolytic tannins, condensed tannins, total tannins, and total saponins in the *Caragana korshinskii* Kom. raw material are 2.30 g/kg DM, 5.52 g/kg DM, 7.67 g/kg DM, and 141.53 g/kg DM, respectively. Contents of hydrolytic tannins, condensed tannins, total tannins, and total saponins in the *Moringa oleifera* Lam. raw material are 0.15 g/kg DM, 9.54 g/kg DM, 9.69 g/kg DM, and 51.41 g/kg DM, respectively.

Anti-nutritional factor contents in *Caragana korshinskii* Kom, and *Moringa oleifera* Lam. each after silage are shown in Table 10. Compared with the raw materials, the addition of P91 significantly reduces the contents of condensed tannins, total tannins, and total saponins in the *Caragana korshinskii* Kom, and *Moringa oleifera* Lam. raw materials (P<0.05). Compared with CK (silage produced after 90 d of silage without an additive), the addition of P91 significantly reduces the contents of hydrolytic tannins, condensed tannins, total tannins, and total saponins in *Caragana korshinskii* Kom., and corresponding degradation rates are 41.94%, 14.48%, 26.60%, and 47.19%, respectively (P<0.05). The addition of P91 reduces the contents of hydrolytic tannins, condensed tannins, total tannins, and total saponins in *Moringa oleifera* Lam., and corresponding degradation rates are 8.81%, 33.51%, 28.33%, and 72.51%, respectively (P<0.05). Therefore, the *Lactiplantibacillus plantarum* P91, as a novel additive for effectively degrading anti-nutritional factors (tannins and total saponins) in a feed, can significantly improve a quality of *Caragana korshinskii* Kom, and *Moringa oleifera* Lam. silage.

TABLE 9

Anti-nutritional components in *Caragana korshinskii* Kom. and *Moringa oleifera* Lam. raw materials

| Item | *Caragana korshinskii* Kom. | *Moringa oleifera* Lam. |
|---|---|---|
| DMs (g/kg FM) | 635.85 ± 2.88 | 203.86 ± 3.63 |
| Hydrolytic tannins (g/kg DM) | 2.15 ± 0.03 | 0.15 ± 0.03 |
| Condensed tannins (g/kg DM) | 5.52 ± 0.47 | 9.54 ± 1.53 |
| Total tannins (g/kg DM) | 7.67 ± 0.43 | 9.69 ± 1.56 |
| Total saponins (g/kg DM) | 141.53 ± 6.35 | 51.41 ± 21.86 |

TABLE 10

Impacts of additives P91 and P87 on tannins and total saponins in *Caragana korshinskii* Kom. and *Moringa oleifera* Lam. Silage

| Index | Material | CK | P91 | P87 |
|---|---|---|---|---|
| Hydrolytic tannins (g/kg DM) | *Caragana korshinskii* Kom. | 4.65 ± 0.74 a | 2.70 ± 0.41 b | 4.34 ± 0.31 a |
| | *Moringa oleifera* Lam. | 2.61 ± 0.77 a | 2.38 ± 0.51 a | 2.37 ± 0.63 a |
| Condensed tannins (g/kg DM) | *Caragana korshinskii* Kom. | 5.80 ± 0.39a | 4.96 ± 0.25 a | 4.97 ± 0.41 a |
| | *Moringa oleifera* Lam. | 9.70 ± 1.86 a | 6.45 ± 0.81 b | 6.61 ± 0.36 b |
| Total tannins (g/kg DM) | *Caragana korshinskii* Kom. | 10.45 ± 1.11 a | 7.67 ± 0.65 b | 9.31 ± 0.47 a |
| | *Moringa oleifera* Lam. | 12.32 ± 2.21 a | 8.83 ± 1.15 b | 8.98 ± 0.83 b |
| Total saponins (g/kg DM) | *Caragana korshinskii* Kom. | 126.59 ± 29.93 a | 66.85 ± 6.74 b | 113.35 ± 9.23 a |
| | *Moringa oleifera* Lam. | 88.89 ± 30.16 a | 24.44 ± 4.39 b | 49.74 ± 10.21 b |

It can be seen from the above analysis that amounts of total tannins and total saponins degraded by the *Lactiplantibacillus plantarum* P91 are greater than amounts of total tannins and total saponins degraded by the *Lactiplantibacillus plantarum* P87. Therefore, the *Lactiplantibacillus plantarum* P91, as a novel silage additive, can significantly improve a quality of silage fermentation.

The above are merely preferred specific implementations of the present disclosure, but the protection scope of the present disclosure is not limited thereto. Any modification or replacement easily conceived by those skilled in the art within the technical scope of the present disclosure should fall within the protection scope of the present disclosure.

The invention claimed is:

1. *Lactiplantibacillus plantarum* P91 with accession number of CGMCC No. 27567;
   wherein the *Lactiplantibacillus plantarum* P91 comprises 16S rDNA shown in SEQ ID NO: 1;
   wherein the *Lactiplantibacillus plantarum* P91 is isolated from *Broussonetia papyrifera* silage;
   wherein the *Lactiplantibacillus plantarum* P91 can reduce anti-nutritional factors in silage and is used for preparation of silage.

2. Silage comprising the *Lactiplantibacillus plantarum* P91 with an accession number of CGMCC No. 27567.

3. The silage according to claim 2, further comprises at least one of *Caragana korshinskii* Kom. silage and *Moringa oleifera* Lam. silage.

4. A preparation method of silage, comprising: mixing a silage raw material with the *Lactiplantibacillus plantarum* P91 with an accession number of CGMCC No. 27567, and allowing fermentation to obtain the silage.

5. The preparation method of silage according to claim 4, wherein a mass ratio of the *Lactiplantibacillus plantarum* P91 to the silage raw material is $1.0 \times 10^5$ CFU/g to $2.0 \times 10^6$ CFU/g.

6. The preparation method of silage according to claim 4, wherein the silage raw material comprises at least one of *Caragana korshinskii* Kom. and *Moringa oleifera* Lam.

* * * * *

SEQUENCE LISTING

```
Sequence total quantity: 2
SEQ ID NO: 1           moltype = DNA  length = 1410
FEATURE                Location/Qualifiers
source                 1..1410
                       mol_type = other DNA
                       organism = synthetic construct
SEQUENCE: 1
accccaccga ctttgggtgt tacaaactct catggtgtga cgggcggtgt gtacaaggcc    60
cgggaacgta ttcaccgcgg catgctgatc cgcgattact agcgattccg acttcatgta   120
ggcgagttgc agcctacaat ccgaactgag aatggcttta agagattagc ttactctcgc   180
gagttcgcaa ctcgttgtac catccattgt agcacgtgtg tagcccaggt cataaggggc   240
atgatgattt gacgtcatcc ccaccttcct ccggtttgtc accggcagtc tcaccagagt   300
gcccaactta atgctggcaa ctgataataa gggttgcgct cgttgcggga cttaacccaa   360
catctcacga cacgagctga cgacaaccat gcaccacctg tatccatgtc ccgaaggga    420
acgtctaatc tcttagattt gcatagtatg tcaagacctg gtaaggttct tcgcgtagct   480
tcgaattaaa ccacatgctc caccgcttgt gcgggccccc gtcaattcct ttgagtttca   540
gccttgcggc cgtactcccc aggcggaatg cttaatgcgt tagctgcagc actgaagggc   600
ggaaaccctc caacacttag cattcatcgt ttacgtatg gactaccagg gtatctaatc   660
ctgtttgcta cccatacttt cgagcctcag cgtcagttac agaccagaca gccgccttcg   720
ccactggtgt tcttccatat atctacgcat ttcaccgcta cacatggagt tccactgtcc   780
tcttctgcac tcaagtttcc cagtttccga tgcacttcct cggttgagcc gaaggcttc   840
acatcagact taaaaaaccg cctgcgctcg ctttacgccc aataaatccg gacaacgctt   900
gccacctacg tattaccgcg gctgctggca cgtagttagc cgtggctttc tggttaaata   960
ccgtcaatac ctgaacagtt actctcagat atgttcttct ttaacaacag agttttacga  1020
gccgaaaccc ttcttcactc acgcggcgtt gctccatcag actttcgtcc attgtggaag  1080
attccctact gctgcctccc gtaggagttt gggccgtgtc tcagtcccaa tgtggccgat  1140
taccctctca ggtcggctac gtatcattgc catggtgagc cgttacccca ccatcctagct 1200
aatacgccgc gggaccatcc aaaagtgata gccgaagcca tctttcaagc tcggaccatg  1260
cggtccaagt tgttatgcgg tattagcatc tgtttccagg tgttatcccc cgcttctggg  1320
caggtttccc acgtgttact caccagttcg ccactcactc aaatgtaaat catgatgcaa  1380
gcaccaatca ataccagagt tcgttcgact                                    1410

SEQ ID NO: 2           moltype = DNA  length = 1425
FEATURE                Location/Qualifiers
source                 1..1425
                       mol_type = other DNA
                       organism = synthetic construct
SEQUENCE: 2
ggttcctaaa aggttaccc accgactttg ggtgttacaa actctcatgg tgtgacgggc     60
ggtgtgtaca aggcccggga acgtattcac cgcggcatgc tgatccgcga ttactagcga   120
ttccgacttc atgtaggcga gttgcagcct acaatccgaa ctgagaatgg ctttaagaga   180
ttagcttact ctcgcgagtt cgcaactcgt gtaccatcc attgtagcac gtgtgtagcc    240
caggtcataa ggggcatgat gatttgacgt catccccacc ttcctccggt ttgtcaccgg   300
cagtctcacc agagtgccca acttaatgct ggcaactgat aataagggtt gcgctcgttg   360
cgggacttaa cccaacatct cacgacacga gctgacgaca accatgcacc acctgtatcc   420
atgtccccga agggaacgtc taatctctta gatttgcata gtatgtcaag acctggtaag   480
gttcttcgcg tagcttcgaa ttaaaccaca tgctccaccg cttgtgcggg ccccgtcaa   540
ttcctttgag tttcagcctt gcggccgtac tccccaggcg gaatgcttaa tgcgttagct   600
gcagcactga agggcggaaa cctccaaca cttagcattc atcgtttacg gtatggacta   660
ccagggtatc taatcctgtt tgctacccat actttcgagc ctcagcgtca gttacagacc   720
agacagccgc cttcgccact ggtgttcttc catatatcta cgcatttcac cgctacacat   780
ggagttccac tgtcctcttc tgcactcaag tttcccagtt tccgatgcac ttcttcggtt   840
gagccgaagg ctttcacatc agacttaaaa aaccgcctgc gctcgcttta cgcccaataa   900
atccggacaa cgcttgccac ctacgtatta ccgcggctgc tggcacgtag ttagccgtgg   960
ctttctggtt aaataccgtc aatacctgaa cagttactct cagatatgtt cttcttttaac  1020
aacagagttt tacgagccga aaccttctt cactcacgcg gcgttgctcc atcagacttt  1080
cgtccattgt ggaagattcc ctactgctgc ctcccgtagg agtttgggcc gtgtctcagt  1140
cccaatgtgg ccgattaccc tctcaggtcg gctacgtatc attgccatgg tgagccgtta  1200
ccccaccatc tagctaatac gccgcgggac catccaaaag tgatagccga agccatcttt  1260
caaactcgga ccatgcggtc caagttgtta tgcggtatta gcatctgttt ccaggtgtta  1320
tcccccgctt ctgggcaggt ttccacgtg ttactcacca gttcgccact cactcaaatg  1380
taaatcatga tgcaagcacc aatcaatacc agagttcgtt cgact                   1425
```